United States Patent [19]

Gehring et al.

[11] Patent Number: 4,695,308
[45] Date of Patent: Sep. 22, 1987

[54] HERBICIDAL SUBSTITUTED 5-AMINO-1-ARYL-PYRAZOLES

[75] Inventors: Reinhold Gehring, Wuppertal; Markus Lindig, Hilden; Otto Schallner, Monheim; Hans-Joachim Santel, Leverkusen; Robert R. Schmidt, Bergisch Gladbach; Jörg Stetter, Wuppertal, all of Fed. Rep. of Germany

[73] Assignee: Bayer Aktiengesellschaft, Leverkusen, Fed. Rep. of Germany

[21] Appl. No.: 925,845

[22] Filed: Oct. 30, 1986

[30] Foreign Application Priority Data

Nov. 5, 1985 [DE] Fed. Rep. of Germany ....... 3539844

[51] Int. Cl.$^4$ .......................... A01N 57/32; C07F 9/65
[52] U.S. Cl. ........................................... 71/86; 71/87; 546/22; 546/14; 548/115
[58] Field of Search ................... 546/22, 24; 548/115; 71/86, 87

[56] References Cited

FOREIGN PATENT DOCUMENTS 0037497 10/1981 European Pat. Off. .
0139182  5/1985 European Pat. Off. .
0154115  9/1985 European Pat. Off. .
3226513  2/1983 Fed. Rep. of Germany .

Primary Examiner—Richard L. Raymond
Attorney, Agent, or Firm—Sprung Horn Kramer & Woods

[57] ABSTRACT

Herbicidally active substituted 5-amino-1-aryl-pyrazoles of the formula

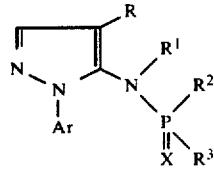

in which R represents hydrogen, cyano, nitro or alkoxycarbonyl, $R^1$ represents hydrogen or alkyl, $R^2$ and $R^3$ independently of one another in each case represent alkyl, alkenyl, alkinyl, halogenoalkyl, alkoxyalkyl, cycloalkyl, alkoxy or cycloalkoxy, or represent in each case optionally substituted aryl, aryloxy, aralkyl or aralkyloxy, X represents oxygen or sulphur and Ar represents in each case optionally substituted phenyl or pyridyl, or salts thereof.

8 Claims, No Drawings

HERBICIDAL SUBSTITUTED 5-AMINO-1-ARYL-PYRAZOLES

The invention relates to new substituted 5-amino-1-aryl-pyrazoles, several processes for their preparation and their use as herbicides.

It is already known that certain substituted 5-amino-1-aryl-pyrazoles, such as, for example, 4-cyano-5-propionamido-1-(2,4,6-trichlorophenyl)-pyrazole, have herbicidal properties, and in particular also selectively herbicidal properties (compare, for example, DE-OS (German Published Specification) 3,226,513).

The herbicidal activity of these already known 5-amino-1-aryl-pyrazoles against weeds, however, like their tolerance towards important crop plants, is not always completely satisfactory in all fields of use.

New substituted 5-amino-1-aryl-pyrazoles of the general formula (I)

$$(I)$$

in which
 R represents hydrogen, cyano, nitro or alkoxycarbonyl,
 $R^1$ represents hydrogen or alkyl,
 $R^2$ and $R^3$ independently of one another in each case represent alkyl, alkenyl, alkinyl, halogenoalkyl, alkoxyalkyl, cycloalkyl, alkoxy or cycloalkoxy, or represent in each case optionally substituted aryl, aryloxy, aralkyl or aralkyloxy,
 X represents oxygen or sulphur and
 Ar represents in each case optionally substituted phenyl or pyridyl,
have been found. The present invention also relates to salts of 5-amino-1-aryl-pyrazoles of the formula (I), for example alkali metal, alkaline earth metal and transition metal salts.

It has furthermore been found that the new substituted 5-amino-1-aryl-pyrazoles of the general formula (I)

$$(I)$$

in which
 R represents hydrogen, cyano, nitro or alkoxycarbonyl,
 $R^1$ represents hydrogen or alkyl,
 $R^2$ and $R^3$ independently of one another in each case represent alkyl, alkenyl, alkinyl, halogenoalkyl, alkoxyalkyl, cycloalkyl, alkoxy or cycloalkoxy, or represent in each case optionally substituted aryl, aryloxy, aralkyl or aralkyloxy,
 X represents oxygen or sulphur and
 Ar represents in each case optionally substituted phenyl or pyridyl, are obtained by one of the processes described below:

(A) the substituted 5-amino-1-aryl-pyrazoles of the formula (I)

$$(I)$$

in which
 R, $R^1$, $R^2$, $R^3$, X and Ar have the abovementioned meanings,
are obtained by a process in which 5-amino-1-aryl-pyrazoles of the formula (II)

$$(II)$$

in which
 R, $R^1$ and Ar have the abovementioned meanings,
are reacted with phosphorus halide compounds of the formula (III)

$$(III)$$

in which
 $R^2$, $R^3$ and X have the abovementioned meanings and
 Hal represents halogen,
if appropriate in the presence of a diluent and if appropriate in the presence of an acid-binding agent;

(B) substituted 5-amino-1-aryl-pyrazoles of the formula (Ia);

$$(Ia)$$

in which
 R, $R^2$, $R^3$, X and Ar have the abovementioned meanings and
 $R^{1-1}$ represents alkyl,
are alternatively obtained by a process in which the substituted 5-amino-1-aryl-pyrazoles obtainable by process (A), of the formula (Ib)

$$(Ib)$$

in which

R, $R^2$, $R^3$, X and Ar have the abovementioned meanings, are reacted with alkylating agents of the formula (IV)

  (IV)

in which $R^{1-1}$ represents alkyl and

A represents an electron-attracting leaving group, if appropriate in the presence of a diluent, if appropriate in the presence of an acid-binding agent and if appropriate in the presence of a catalyst;

(C) 4-nitro-1-aryl-pyrazoles of the formula (Ic)

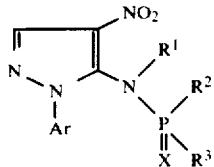  (Ic)

in which $R^1$, $R^2$, $R^3$ and Ar have the abovementioned meanings, are obtained by a process in which the 1-aryl-pyrazoles unsubstituted in the 4-position obtainable by process (A) or (B), of the formula (Id)

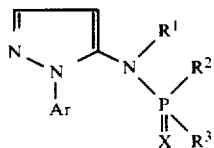  (Id)

in which $R^1$, $R^2$, $R^3$, X and Ar have the abovementioned meanings, are reacted with nitric acid, if appropriate in the presence of a diluent and if appropriate in the presence of a catalyst. Salts are obtained by a process in which the 5-amino-1-arylpyrazoles of the formula (I) in which $R^1$ represents hydrogen are reacted with an inorganic metal salt, e.g. sodium chloride, calcium chloride, barium chloride or copper sulphate, in usual and general known manner.

Finally, it has been found that the new substituted 5-amino-1-aryl-pyrazoles of the formula (I) have herbicidal properties, and in particular also selective herbididal properties.

Surprisingly, the substituted 5-amino-1-arylpyrazoles of the general formula (I) according to the invention exhibit a considerably better generally herbicidal activity against weeds, and moreover also a considerably greater tolerance towards important crop plants than the 5-amino-1-aryl-pyrazoles known from the prior art, such as, for example, 4-cyano-5-propionamido-1-(2,4,6-trichlorophenyl)-pyrazole, which are closely related compounds chemically and from the point of view of their action.

Formula (I) provides a general definition of the substituted 5-amino-1-aryl-pyrazoles according to the invention. Preferred compounds of the formula (I) are those in which R represents hydrogen, cyano or nitro, or represents straight-chain or branched alkoxycarbonyl with 1 to 4 carbon atoms, $R^1$ represents hydrogen, or represents straight-chain or branched alkyl with 1 to 6 carbon atoms, $R^2$ and $R^3$ independently of one another represent in each case straight-chain or branched alkyl, alkenyl or alkinyl with in each case up to 8 carbon atoms, or represent straight-chain or branched halogenoalkyl with 1 to 6 carbon atoms and 1 to 13 identical or different halogen atoms, or represent straight-chain or branched alkoxyalkyl with in each case 1 to 4 carbon atoms in the individual alkyl parts, or represent straight-chain or branched alkoxy with 1 to 6 carbon atoms, or represent cycloalkyl or cycloalkyloxy with in each case 3 to 7 carbon atoms, or represent aryl, aryloxy, aralkyl or aralkyloxy with in each case 6 to 10 carbon atoms in the individual aryl parts and, where appropriate, one to three carbon atoms in the straight-chain or branched alkyl parts, in each case optionally monosubstituted or polysubstituted in the aryl part by identical or different substituents, possible substituents on the aryl in each case being: halogen, cyano, nitro and in each case straight-chain or branched alkyl, alkoxy, alkylthio or halogenoalkyl with in each case 1 to 4 carbon atoms and, in the case of the halogenoalkyl, with 1 to 9 identical or different halogen atoms, X represents oxygen or sulphur and Ar represents phenyl, 2-pyridyl, 3-pyridyl or 4-pyridyl, in each case optionally monosubstituted or polysubstituted by identical or different substituents, possible substituents in each case being: cyano, nitro, halogen, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms or the radical —$S(O)_n$—$R^4$, wherein $R^4$ represents amino, or represents in each case straight-chain or branched alkyl, alkylamino, dialkylamino or halogenoalkyl with in each case 1 to 4 carbon atoms in the individual alkyl parts and, in the case of the halogenoalkyl, with 1 to 9 identical or different halogen atoms, and n represents the number 0, 1 or 2, and alkali metal salts thereof.

Particularly preferred compounds of the formula (I) are those in which

R represents hydrogen, cyano, nitro, methoxycarbonyl or ethoxycarbonyl, $R^1$ represents hydrogen, methyl, ethyl, n- or i-propyl, or n-, i- or s-butyl, $R^2$ and $R^3$ independently of one another each represent methyl, ethyl, n- or i-propyl, n-, i-, s- or t-butyl, allyl, propargyl, chloromethyl, dichloromethyl, trichloromethyl, fluoromethyl, dichlorofluoromethyl, trifluoromethyl, dichlorofluoromethyl, difluorochloromethyl, chloroethyl, trichloroethyl, pentachloroethyl, trifluoroethyl, pentafluoroethyl, bromoethyl, methoxymethyl, methoxyethyl, ethoxymethyl, ethoxyethyl, n-propoxymethyl, i-propoxymethyl, n-propoxyethyl, i-propoxyethyl, methoxy, ethoxy, n- or i-propoxy, n-, i-, s- or t-butoxy, cyclopropyl, cyclopentyl, cyclohexyl or cyclohexyloxy, or represent benzyl, benzyloxy, phenyl or phenoxy, in each case optionally mono-, di-, tri-, tetra- or pentasubstituted by identical or different substituents, possible substituents on the aryl in each case being: fluorine, chlorine, bromine, cyano, nitro, methyl, ethyl, methoxy, methylthio or trifluoromethyl, X represents oxygen or sulphur and Ar represents phenyl which is optionally mono-, di-, tri-, tetra- or pentasubstituted by identical or different substituents, or represents 2-pyridyl which is optionally mono-, di-, tri- or tetrasubstituted by identical or different substituents, possible substituents in each case being: cyano, nitro, fluorine, chlorine, bomine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroerthoxy, trifluoroethoxy, difluorodichloroethoxy, trifluorodichloroethoxy, pentachloroethoxy or the radical —S(O)$_n$—R$^4$, wherein R$^4$ represents amino, methylamino, ethylamino, dimethylamino, diethylamino, fluorodichloromethyl, difluoromethyl, tetrafluoroethyl, trichloroethyl, trifluoromethyl, methyl or ethyl and n represents the number 0, 1 or 2.

The following substituted 5-amino-1-aryl-pyrazoles of the general formula (I) may be mentioned specifically, in addition to the compounds mentioned in the preparation examples:

TABLE 1

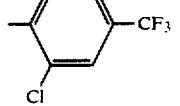

(I)

| R | R$^1$ | R$^2$ | R$^3$ | X | Ar |
|---|---|---|---|---|---|
| NO$_2$ | H | CH$_3$ | CH$_3$ | O | 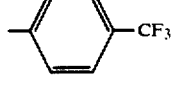 |
| NO$_2$ | H | CH$_3$ | CH$_3$ | O | |
| NO$_2$ | H | C$_2$H$_5$ | C$_2$H$_5$ | O |  |
| NO$_2$ | H | CH$_3$ | —CH$_2$Cl | S | 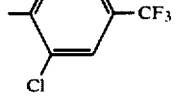 |
| NO$_2$ | H | —OCH$_3$ | CH$_3$ | O | 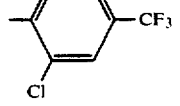 |

TABLE 1-continued (I)

Structure: pyrazole with substituents R (position 4), N-Ar (N1), and at position 5: N(R¹)-P(=X)(R²)(R³)

| R | R¹ | R² | R³ | X | Ar |
|---|----|----|----|---|----|
| NO₂ | H | —O—C₆H₅ | CH₃ | O | 2,6-dichloro-4-(trifluoromethyl)phenyl |
| NO₂ | CH₃ | —O—C₆H₅ | CH₃ | O | 2,4-dichlorophenyl |
| NO₂ | H | —OCH₃ | —OCH₃ | O | 3-chloro-5-(trifluoromethyl)pyridin-2-yl |
| NO₂ | H | CH₃ | —CH₃ | O | 3-chloro-5-(trifluoromethyl)pyridin-2-yl |
| NO₂ | CH₃ | —OC₂H₅ | —OC₂H₅ | O | 3-chloro-4-(trifluoromethyl)phenyl |
| NO₂ | H | CH₃ | CH₃ | O | 2-bromo-4-(trifluoromethyl)phenyl |
| NO₂ | H | CH₃ | —OC₂H₅ | S | 2-bromo-4-(trifluoromethyl)phenyl |
| NO₂ | H | CH₃ | —C₆H₅ | O | 2-bromo-4-(trifluoromethyl)phenyl |
| NO₂ | H | —OC₂H₅ | —OC₂H₅ | O | 2-bromo-4-(trifluoromethyl)phenyl |

TABLE 1-continued
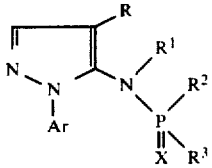
(I)
| R | R¹ | R² | R³ | X | Ar |
|---|---|---|---|---|---|
| NO₂ | H | CH₃ | —OC₂H₅ | S | 2,6-Cl₂-4-CF₃-phenyl (Cl,Cl,CF₃,Cl) 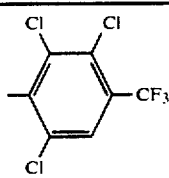 |
| NO₂ | H | phenyl 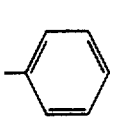 | phenyl 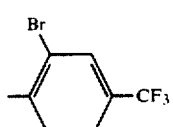 | O | 2-Br-4-CF₃-phenyl 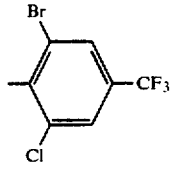 |
| NO₂ | H | CH₃ | —OC₂H₅ | O | 2-Br-6-Cl-4-CF₃-phenyl 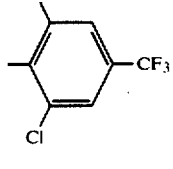 |
| NO₂ | H | —OC₂H₅ | —OC₂H₅ | S | 2-Br-6-Cl-4-CF₃-phenyl 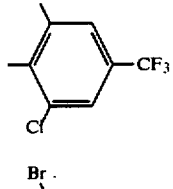 |
| NO₂ | H | phenyl  | CH₃ | O | 2-Br-6-Cl-4-CF₃-phenyl 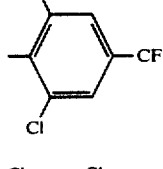 |
| NO₂ | H | phenyl 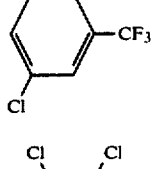 | pyridyl 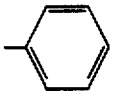 | O | 2-Br-6-Cl-4-CF₃-phenyl 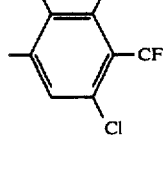 |
| CN | H | C₂H₅ | —OCH₃ | O | 2,6-Cl₂-4-CF₃-phenyl |
| CN | H | CH₃ | phenyl | O | 2,6-Cl₂-4-CF₃-phenyl |

TABLE 1-continued

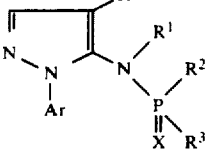

(I)

| R | R¹ | R² | R³ | X | Ar |
|---|----|----|----|---|----|
| CN | H | CH₃ | 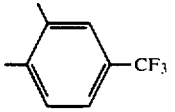 | O | 2-Cl, 4-CF₃-phenyl |
| CN | H | CH₃ | —OC₂H₅ | O | 2-Br, 4-CF₃-phenyl |
| CN | H | CH₃ | —OCH₃ | S | 2,4-Cl₂, 5-Cl, 3-CF₃-phenyl (2,4,5-trichloro-3-trifluoromethylphenyl) |
| CN | H | CH₃ | 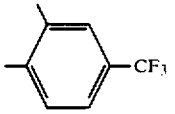 | O | 2-Cl, 4-CF₃, 6-Br-phenyl |
| CN | H | phenyl | phenyl | O | 2,3-Cl₂, 5-Cl, 4-CF₃-phenyl |
| CN | H | CH₃ | 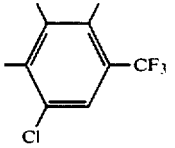 | O | 3-Cl, 5-CF₃-pyridyl |
| CN | H | —OC₂H₅ | —OC₂H₅ | S | 2,3-Cl₂, 5-Cl, 4-CF₃-phenyl |

If, for example, 5-amino-4-cyano-1-(2,6-dichloro-4-trifluoromethylphenyl)-pyrazole and O,O-diethyl-thiophosphoryl chloride are used as starting substances, the course of the reaction in process (A) according to the invention can be represented by the following equation:

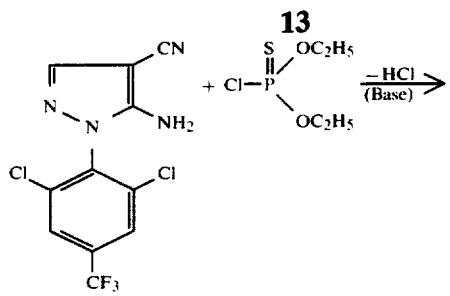
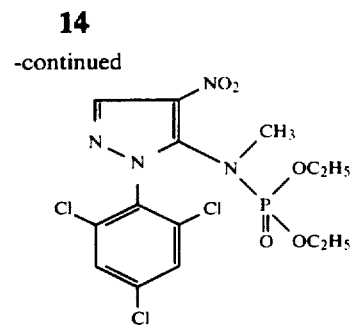

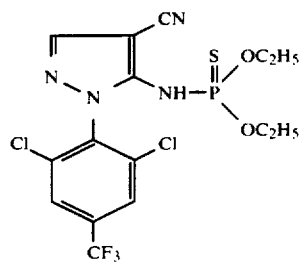

If, for example, 5-(O,O-diethyl-phosphorylamino)-4-nitro-1-(2,6-dichloro-4-trifluoro-methyl-phenyl)-pyrazole and methyl iodide are used as starting substances, the course of the reaction in process (B) according to the invention can be represented by the following equation:

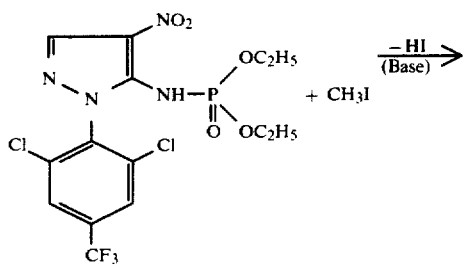

If, for example, 5-[N-methyl-N-(O,O-diethylphosphoryl)-amino]-1-(2,4,6-trichlorophenyl)-pyrazole and nitric acid are used as starting substances, the course of the reaction in process (C) according to the invention can be represented by the following equation:

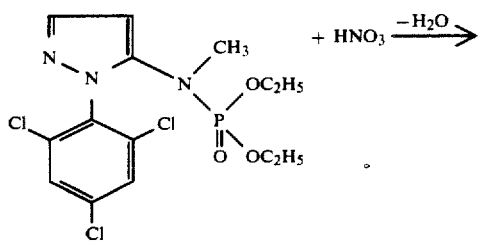

Formula (II) provides a general definition of the 5-amino-1-aryl-pyrazoles required as starting substances for carrying out process (A) according to the invention. In this formula (II), R, $R^1$ and Ar preferably represent those radicals which have already been mentioned as preferred for these substituents in connection with the description of the substances of the formula (I) according to the invention.

The 5-amino-1-aryl-pyrazoles of the formula (II) are known in some cases (compare, for example, EP-OS (European Published Specification) 26,034, EP-OS (European Published Specification) 34,945, EP-OS (European Published Specification) 53,678, DE-OS (German Published Specification) 3,226,496, DE-OS (German Published Specification) 3,226,513, DE-OS (German Published Specification) 3,129,429, DE-OS (German Published Specification) 3,325,488, DE-OS (German Published Specification) 3,408,727, DE-OS (German Published Specification) 3,420,985 and DE-OS (German Published Specification) 3,402,308); and some of them are the subject of commonly assigned application Ser. No. 754,048, filed July 11, 1985, now pending, application Ser. No. 866,638, filed May 22, 1986, now pending, and application Ser. No. 866,049, filed May 22, 1986, now pending, corresponding respectively to German Pat. No. 3,426,424 of July 18, 1984, German Pat. No. 3,520,330 of June 7, 1985 and German Pat. No. 3,520,327 of June 7, 1985 and can be obtained by processes analogous to known processes.

Formula (III) provides a general definition of the phosphorus halide compounds furthermore required as starting substances for carrying out process (A) according to the invention. In this formula (III), $R^2$, $R^3$ and X preferably represent those radicals which have already been mentioned as preferred for these substituents in connection with the description of the substances of the formula (I) according to the invention.

Hal preferably represents chlorine or bromine. The phosphorus halide compounds of the formula (III) are generally known compounds of organic chemistry.

Formula (Ib) provides a general definition of the substituted 5-amino-1-aryl-pyrazoles required as starting substances for carrying out process (B) according to the invention. In this formula (Ib), R, $R^2$, $R^3$, Ar and X preferably represent those radicals which have already been mentioned as preferred for these substituents in connection with the description of the substances of the formula (I) according to the invention.

The substituted 5-amino-1-aryl-pyrazoles of the formula (Ib) are compounds according to the invention and are obtainable with the aid of processes (A) and (C) according to the invention.

Formula (IV) provides a general definition of the alkylating agents furthermore required as starting substances for carrying out process (B) according to the invention. In this formula (IV), $R^{1-1}$ preferably represents those radicals which have already been mentioned as preferred for the substituent $R^1$ in connection with the description of the substances of the formula (I) according to the invention, with the exception of the hydrogen radical.

A preferably represents halogen, in particular chlorine, bromine or iodine, or represents in each case optionally substituted alkylsulphonyloxy, alkoxysulphonyloxy or arylsulphonyloxy, such as, for example, methanesulphonyloxy, methoxysulphonyloxy or p-toluenesulphonyloxy.

The alkylating agents of the formula (IV) are generally known compounds of organic chemistry.

Formula (Id) provides a general definition of the 1-aryl-pyrazoles unsubstituted in the 4-position which are required as starting substances for carrying out process (C) according to the invention. In this formula (Id), $R^1$, $R^2$, $R^3$, Ar and X preferably represent those radicals which have already been mentioned as preferred for these substituents in connection with the description of the substances of the formula (I) according to the invention.

The 1-aryl-pyrazoles unsubstituted in the 4-position, of the formula (Id), are compounds according to the invention and are obtainable with the aid of processes (A) or (B) according to the invention.

Possible diluents for carrying out process (A) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

Process (A) according to the invention is preferably carried out in the presence of a suitable acid-binding agent.

Possible acid-binding agents are all the customary inorganic or organic bases. These include, for example, alkali metal hydroxides, hydrides or amides, such as sodium hydroxide or potassium hydroxide, sodium hydride or sodium amide, alkali metal carbonates or alcoholates, such as sodium methylate or ethylate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

If an amine in liquid form is used as the acid-binding agent, it is also possible for this to be simultaneously employed, in a corresponding excess, as the diluent. The addition of other diluents may in this case be unnecessary.

The reaction temperatures can be varied within a substantial range in carrying out process (A) according to the invention. The reaction is in general carried out at temperatures between $-80°$ C. and $+120°$ C., preferably at temperatures between $-70°$ C. and $+70°$ C.

For carrying out process (A) according to the invention, in general 1.0 to 3.0 moles, preferably 1.0 to 2.0 moles, of phosphorus halide compound of the formula (III) and 1.0 to 3.0 moles, preferably 1.0 to 2.0 moles, of acid-binding agent are employed per mole of 5-amino-1-aryl-pyrazole of the formula (II). The reaction is carried out and the reaction products of the formula (I) are worked up and isolated by generally customary processes.

Possible diluents for carrying out process (B) according to the invention are likewise inert organic solvents.

These include, in particular, aliphatic or aromatic hydrocarbons, such as, for example, benzine, benzene, toluene, xylene, petroleum ether, hexane and cyclohexane, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hxamethylphosphoric acid triamide, or esters, such as ethyl acetate.

If appropriate, process (B) according to the invention can be carried out in a two-phase system, such as, for example, water/toluene or water/methylene chloride, if appropriate in the presence of a phase transfer catalyst. Examples of such catalysts which may be mentioned are: tetrabutylammonioum iodide, tetrabutylammonium bromide, tributyl-methylphosphonium bromide, trimethyl-$C_{13}$/$C_{15}$-alkylammonium chloride, dibenzylammonium methyl-sulphate, dimethyl-$C_{12}$/$C_{14}$-alkyl-benzylammonium chloride, tetrabutylammonium hydroxide, 15-crown-5-, 18-crown-6, triethylbenzylammonium chloride and trimethylbenzylammonium chloride.

Possible acid-binding agents for carrying out process (B) according to the invention are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (B) according to the invention. The reaction is in general carried out at temperatures between $-20°$ C. and $+150°$ C., preferably at temperatures between $0°$ C. and $100°$ C.

For carrying out process (B) according to the invention, in general 1.0 to 50.0 moles, preferably 1.0 to 25.0 moles, of alkylating agent of the formula (IV) and, if appropriate, 1.0 to 50.0 moles of acid-binding agent and, if appropriate, 0.01 to 1.0 mole of phase transfer catalyst are employed per mole of substituted 5-amino-1-aryl-pyrazole of the formula (Ib). The reaction is carried out and the reaction products of the formula (Ia) are worked up and isolated by generally customary processes.

Possible diluents for carrying out process (C) according to the invention are all the solvents which can usually be employed for such nitration reactions. The acids suitable as reagents or mixtures thereof with catalyst acid, such as, for example, sulphuric acid, nitric acid, acetic anhydride or nitrating acid, are preferably simultaneously used as the diluent. If appropriate, inert organic solvents, such as, for example, glacial acetic acid or chlorinated hydrocarbons, such as methylene chloride, chloroform or carbon tetrachloride, are also possible diluents.

Possible catalysts or reaction auxiliaries for carrying out process (C) according to the invention are likewise the catalyst customary for such nitration reactions; acid catalysts, such as, for example, sulphuric acid or acetic anhydride, are preferably used.

The reaction temperatures can be varied within a substantial range in carrying out process (C) according to the invention. The reaction is in general carried out between −50° C. and +20° C., preferably between −20° C. and +150° C.

For carrying out process (C) according to the invention, in general 1.0 to 100 moles, preferably 1.0 to 50 moles, of nitric acid and, if appropriate, 0.1 to 10 moles of catalyst are employed per mole of 1-aryl-pyrazoles unsubstituted in the 4-position, of the formula (Id).

The reaction is carried out and the reaction products of the formula (Ic) are worked up and isolated in the generally customary manner.

It is furthermore also possible to obtain, from the substituted 5-amino-1-aryl-pyrazole-phosphoric or -phosphonic esters according to the invention, of the formula (Ie)

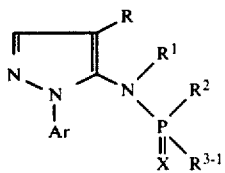

in which
R, R¹, R², X and Ar have the meanings given in the substituent difinition of the compounds of the formula (I) according to the invention and
R³⁻¹ represents alkoxy, cycloalkyloxy, aralkyloxy or aryloxy,
which are obtainable with the aid of processes (A), (B) or (C) according to the invention, to split the phosphorus ester bond(s) with the aid of customary known ester hydrolysis processes, for example by acid or base catalysis, and in this manner to obtain free phosphorus or phosphonic acid derivatives of the formula (V)

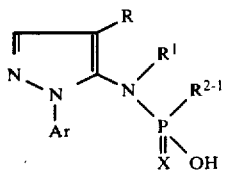

in which
R, R¹, X and Ar have the abovementioned meanings and
R²⁻¹ represents alkyl, alkenyl, alkinyl, halogenoalkyl, alkoxyalkyl or cycloalkyl, or represents in each case optionally substituted aryl or aralkyl, or represents hydroxyl.

From these compounds, corresponding salts with inorganic and organic cations, for example with alkali metal cations, alkaline earth metal cations or transition metal cations or with optionally substituted ammonium or phosphonium ions, can likewise be prepared in the customary and generally known manner.

Both the phosphonic acids and phosphoric acids of the formula (V) and the salts obtainable therefrom (phosphonates or phosphates) have a herbicidal action.

The active compounds according to the invention can be used as defoliants, desiccants, agents for destroying broad-leaved plants and, especially, as weed-killers. By weeds, in the broadest sense, are to be understood all plants which grow in locations whereby they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eluesine, Brachiaria, Lolium, Bromus, Avena, Cyperus, Sorghum, Agropyron, Cynodon, Monochoria, Fimbristylis, Satittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating dicotyledon weeds in monocotyledon and dicotyledon crops, such as, for example, wheat, barley or cotton.

The active compounds according to the invention moreover also have a growth-regulating activity. When applied in appropriate amounts, the active compounds according to the invention also exhibit fungicidal activity, and can be employed, for example, for combating rice diseases, such as, for example, against the causative organism of rice spot disease (Pyricularia oryzae).

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meal, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products, as dispersing agents ther are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazin-2,4(1H,3H)-dione or N-(2-benzothiazolyl-N,N'-dimethyl-urea, for combating weeds in cereals; 4-amino-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one for combating weeds in soy Mixtures with N,N-dimethyl-N'-(3-trifluoromethylphenyl)-urea; N,N-dimethyl-N'-(3-chloro-4-methylphenyl)urea; N,N-dimethyl-N'-(4-isopropylphenyl)-urea; 4-amino-6-t-butyl-3-ethylthio-1,2,4-triazin-5(4H)-one; 2,4-dichlorophenoxyacetic acid; 2,4-dichlorophenoxypropionic acid; (2-methyl-4-chlorophenoxy)-acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; 2-benzyloxyethyl, trimethylsilylmethyl or 2,2-diethoxyethyl 2-[4-(3,5-dichloropyrid-2-yl-oxy)-phenoxy]-propionate; S-(2,3,4-trichloroallyl)N,N-diisopropyl-thiolcarbamate; N-(1-ethylpropyl)-3,4-dimethyl-2,6-dinitroaniline; exo-1-methyl-4-(1-methylethyl)-2-(2-methylphenyl-methoxy)-7-oxabicyclo-(2,2,1)-heptane; 4-ethylamino-2-(1,3-benzothiazol-2-yloxy)-acetanilide; methyl-5-(2,4-dichlorophenoxy)-2-nitrobenzoate; 3,5-diiodo-4-hydroxybenzonitrile; 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; [(4-amino-3,5-dichloro-6-fluoro-2-pyridinyl)-oxy]-acetic acid or acetic acid 1-methylheptyl ester; 3,5-dibromo-4-hydroxy-benzonitrile or methyl 2-[4-(2,4-dichlorophenoxy)-phenoxy]-propionate, where appropriate, are also of advantage. Surprisingly, some mixtures also show a synergistic action.

Mixtures with other known active compounds, such as fungicides, insecticides, acaricides, nematicides, bird repell nts, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

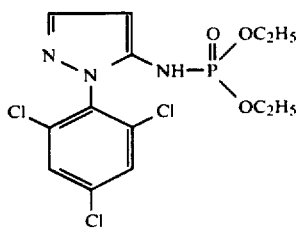

(Process A)

A mixture of 3 g (0.01 mole) of 5-amino-1-(2,4,6-trichloro-phenyl)-pyrazole (compare U.S. application Ser. No. 690,347, filed Jan. 10, 1985, now pending), 1.7 g (0.01 mole) of phosphoric acid diethyl ester-chloride and 0.05 g of diazabicyclooctane (DBACO) in 10 ml of pyridine is stirred at room temperature for 15 hours, 50 ml of water are then added, the mixture is filtered and the residue is washed several times with water and then with petroleum ether and dried.

3.1 g (72% of theory) of 5-(O,O-diethyl-phosphorylamino)-1-(2,4,6-trichlorophenyl)-pyrazole of melting point 187° C. are obtained.

EXAMPLE 2

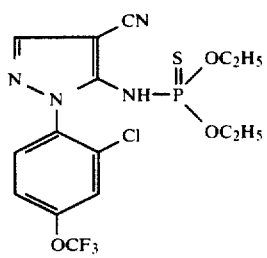

(Process A)

6.1 g (0.02 mole) of 5-amino-4-cyano-1-(2-chloro-4-trifluoromethoxyphenyl)-pyrazole (compare DE-OS (German Published Specification) 3,420,985) are added to a suspension of 1.0 g (0.041 mole) of sodium hydride in 40 ml of dry tetrahydrofuran and, when the evolution of gas has ended, 4.5 g (0.024 mole) of O,O-diethyl-thiophosphoryl chloride in 20 ml of tetrahydrofuran are added. The mixture is stirred at room temperature for 15 hours, a further 1.0 g (0.041 mole) of sodium hydride and 6.5 g (0.02 mole) of O,O-diethyl-thiophosphoryl chloride are aded and the mixture is stirred at room temperature for a further 2 hours. For working up, the solvent is removed in vacuo and the residue is purified by chromatography (silica gel; eluting agent: methylene chloride/ethyl acetate 9:1).

7.3 g (80% of theory) of 4-cyano-5-(O,O-diethylthiophosphorylamino)-1-(2-chloro-4-trifluoromethoxyphenyl)pyrazole of melting point 89°-91° C. are obtained.

EXAMPLE 3

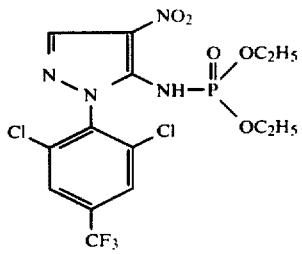

(Process A)

0.5 g (0.02 mole) of sodium hydride (80% pure) are added to 3.4 g (0.01 mole) of 5-amino-4-nitro-1-(2,6-dichloro-4-trifluoromethyl-phenyl)-pyrazole (compare U.S. application Ser. No. 690,347, filed Jan. 10, 1985) in 30 ml of dry tetrahydrofuran at room temperature, and 1.8 g (0.01 mole) of O,O-diethylphosphoryl chloride are then added dropwise. When the addition has ended, the mixture is stirred for a further 30 minutes and concentrated in vacuo, the residue is taken up in chloroform, the mixture is washed with water and dried over sodium sulphate and the solvent is removed in vacuo. The residue is recrystallized from ether/ethanol (9:1).

2.8 g (59% of theory) of 5-(O,O-diethylphosphorylamino)-4-nitro-1-(2,6-dichloro-4-trifluoromethylphenyl)pyrazole of melting point 119° C. are obtained.

EXAMPLE 3

Alternative preparation: Process C 0.7 ml of 98 percent strength nitric acid is added dropwise to 4.3 g (0.01 mole) of 5-(O,O-diethylphosphoryl-amino)-1-(2,6-dichloro-4-trifluoromethyl-phenyl)-pyrazole in 20 ml of concentrated sulphuric acid at 0° C. to 5° C. and, when the addition has ended, the mixture is stirred at room temperature for 1 hour. For working up, the mixture is poured onto 200 ml of ice and extracted with 150 ml of chloroform, the extract is washed several times with saturated sodium bicarbonate solution and dried over magnesium sulphate, and the solvent is removed in vacuo.

2.1 g (44% of theory) of 5-(O,O-diethyl-phosphorylamino)-4-nitro-1-(2,6-dichloro-4-trifluoromethyl-phenyl)pyrazole) of melting point 119° C. are obtained.

EXAMPLE 4

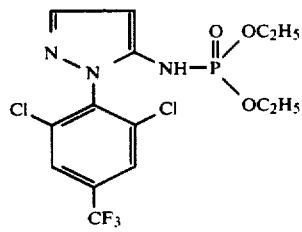

(Process A)

A mixture of 3.3 g (0.01 mole) of 5-amino-1-(2,6-dichloro-4-trifluoromethyl-phenyl)-pyrazole (compare U.S. application Ser. No. 690,347, filed Jan. 10, 1985), 1.7 g (0.01 mole) of phosphoric acid diethyl ester-chloride and 0.05 g of diazabicyclooctane (DABCO) in 10 ml of pyridine is stirred at room temperature for 15 hours, 50 ml of water are then added, the mixture is filtered and the residue is washed several times with water and then with petroleum ether and dried.

3.6 g (75% of theory) of 5-(O,O-diethyl-phosphorylamino)-1-(2,6-dichloro-4-trifluoromethylphenyl)-pyrazole of melting point 175° C. are obtained.

EXAMPLE 5

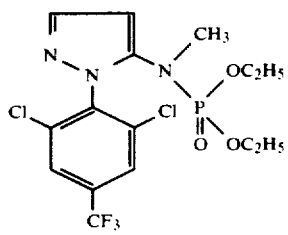

(Process B)

3 g (0.12 mole) of 80% pure sodium hydride are added to 4 g (0.0092 mole) of 5-(O,O-diethylphosphorylamino)-1-(2,6-dichloro-4-trifluoromethylphenyl)-pyrazole in 150 ml of dry tetrahydrofuran, the mixture is heated at the reflux temperature for 30 minutes, 20 ml (0.32 mole) of methyl iodide are then added and the mixture is heated at the reflux temperature for a further 2 hours. For working up, insoluble constituents are filtered off and the filtrate is concentrated in vacuo.

3.2 g (78% of theory) of 5-[N-methyl-N-(O,O-diethylphosphoryl)-amino]-1-(2,6-dichloro-4-trifluoromethylphenyl)-pyrazole are obtained as a viscous oil. $^1$H-NMR (CDCl$_3$, tetramethylsilane) $\delta = 2.95$ ppm.

The following substituted 5-amino-1-aryl-pyrazoles of the general formula (I) are obtained in a corresponding manner and in accordance with the general statements on the preparation:

TABLE 2

| Example No. | R | R$^1$ | R$^2$ | R$^3$ | X | Ar | Melting point/°C. |
|---|---|---|---|---|---|---|---|
| 6 | H | H | CH$_3$ | —OC$_6$H$_5$ | O | 2,4,6-trichloro-phenyl-CF$_3$ | 168 |
| 7 | H | H | CH$_3$ | —C$_6$H$_5$ | O | 2-chloro-4-CF$_3$-phenyl | 110 |
| 8 | H | H | CH$_3$ | —C$_6$H$_5$ | O | 2,4,6-trichloro-phenyl-CF$_3$ | 98 |
| 9 | H | H | CH$_3$ | —CH$_2$Cl | O | 2-chloro-4-CF$_3$-phenyl | 131 |
| 10 | H | H | CH$_3$ | —CH$_2$Cl | O | 2,4,6-trichloro-phenyl-CF$_3$ | 104 |

TABLE 2-continued

General structure (I):

Pyrazole ring with substituent R at position 4, N-Ar at N1, and at position 5 an N(R¹) group bonded to P(=X)(R²)(R³).

| Example No. | R | R¹ | R² | R³ | X | Ar | Melting point/°C. |
|---|---|---|---|---|---|---|---|
| 11 | H | H | CH₃ | —CH₂Cl | O | 2,4,6-trichlorophenyl | 148 |
| 12 | H | H | —OC₂H₅ | —OC₂H₅ | O | 2,3,4-trichlorophenyl | 156 |
| 13 | H | H | CH₃ | phenyl | O | 2,4,6-trichlorophenyl | 176 |
| 14 | H | H | CH₃ | —CH₂Cl | O | 2,4-dichlorophenyl | 136–140 |
| 15 | H | H | CH₃ | —CH₂Cl | O | 2,6-dichloro-4-(SCF₃)phenyl | 147–149 |
| 16 | H | H | CH₃ | —CH₂Cl | O | 2-chloro-4-(OCF₃)phenyl | 104–108 |
| 17 | H | H | CH₃ | —C₂H₅ | O | 2,4-dichlorophenyl | ¹H—NMR: 1.5* |
| 18 | H | H | CH₃ | —OC₂H₅ | O | 2,4-dichlorophenyl | 110–115 |
| 19 | H | H | —OC₂H₅ | —OC₂H₅ | O | 2,4-dichlorophenyl | 76–86 |

TABLE 2-continued
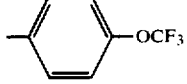
(I)
| Example No. | R | R¹ | R² | R³ | X | Ar | Melting point/°C |
|---|---|---|---|---|---|---|---|
| 20 | H | H | CH₃ | —OC₂H₅ | O | 2-Cl, 4-OCF₃-phenyl | 120–122 |
| 21 | H | H | CH₃ | C₂H₅ | O | 2-Cl, 4-OCF₃-phenyl | ¹H—NMR: 1.5* |
| 22 | H | H | —OC₂H₅ | —OC₂H₅ | O | 2-Cl, 4-OCF₃-phenyl | 77 |
| 23 | H | H | CH₃ | —OCH₃ | S | 2,6-Cl₂, 4-CF₃-phenyl | 118 |
| 24 | NO₂ | H | CH₃ | phenyl | O | 2,6-Cl₂, 4-Cl-phenyl | 164 |
| 25 | NO₂ | H | CH₃ | phenyl | O | 2,6-Cl₂, 4-CF₃-phenyl | 158 |
| 26 | NO₂ | H | CH₃ | phenyl | O | 2-Cl, 4-CF₃-phenyl | 95 |
| 27 | NO₂ | H | CH₃ | —OC₂H₅ | O | 2,6-Cl₂, 4-CF₃-phenyl | 98 |
| 28 | NO₂ | H | —OC₂H₅ | —OC₂H₅ | O | 2,3-Cl₂-phenyl | 103 |

TABLE 2-continued
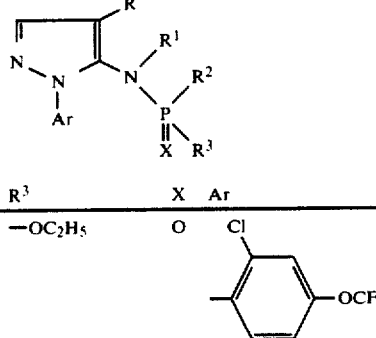
(I)
| Example No. | R | R¹ | R² | R³ | X | Ar | Melting point/°C |
|---|---|---|---|---|---|---|---|
| 29 | $NO_2$ | H | $-OC_2H_5$ | $-OC_2H_5$ | O | 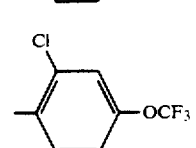 | 94–98 |
| 30 | $NO_2$ | H | $CH_3$ | $-C_2H_5$ | O | 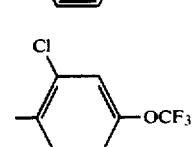 | 145–149 |
| 31 | $NO_2$ | H | $CH_3$ | $-OC_2H_5$ | O | 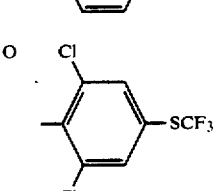 | 153 |
| 32 | $NO_2$ | H | $CH_3$ | $-OC_2H_5$ | O | 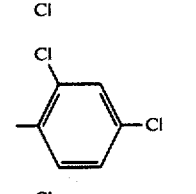 | 162–164 |
| 33 | $NO_2$ | H | $-OC_2H_5$ | $-OC_2H_5$ | O | 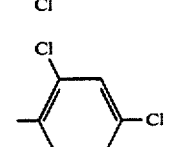 | 128–133 |
| 34 | $NO_2$ | H | $CH_3$ | $-OC_2H_5$ | O | | 149–152 |
| 35 | $NO_2$ | H | $-OC_2H_5$ | $-OC_2H_5$ | O | 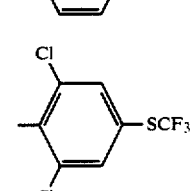 | 100–104 |
| 36 | $NO_2$ | H | $CH_3$ | $C_2H_5$ | O | 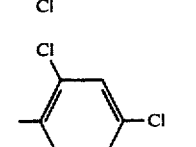 | 141–146 |
| 37 | $NO_2$ | H | $CH_3$ | $-OC_2H_5$ | O | 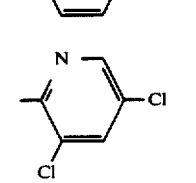 | 142–146 |

TABLE 2-continued (1)

| Example No. | R | R¹ | R² | R³ | X | Ar | Melting point/°C |
|---|---|---|---|---|---|---|---|
| 38 | $NO_2$ | H | $-CH_3$ | $-CH_2Cl$ | O | 2,4,6-trichlorophenyl (Cl, Cl, Cl) | 109 |
| 39 | $NO_2$ | H | $CH_3$ | $-CH_2Cl$ | O | 2,6-dichloro-4-$CF_3$-phenyl | 116 |
| 40 | $NO_2$ | H | $CH_3$ | $-CH_2Cl$ | O | 2-chloro-4-$CF_3$-phenyl | 134 |
| 41 | $NO_2$ | H | $CH_3$ | $-OCH_3$ | S | 2,6-dichloro-4-$CF_3$-phenyl | ¹H—NMR: 1,85* |
| 42 | $NO_2$ | $CH_3$ | $-OC_2H_5$ | $-OC_2H_5$ | O | 2,6-dichloro-4-$CF_3$-phenyl | ¹H—NMR: 3,05* |
| 43 | CN | H | $-OC_2H_5$ | $-OC_2H_5$ | O | 2,6-dichloro-4-$SCF_3$-phenyl | 157-160 |
| 44 | CN | H | $-OC_2H_5$ | $-OC_2H_5$ | S | 2,6-dichloro-4-$CF_3$-phenyl | 125-127 |
| 45 | CN | H | phenyl | phenyl | O | phenyl | 229-231 |

TABLE 2-continued
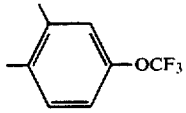
(I)
| Example No. | R | $R^1$ | $R^2$ | $R^3$ | X | Ar | Melting point/°C. |
|---|---|---|---|---|---|---|---|
| 46 | CN | H | $-OC_2H_5$ | $-OC_2H_5$ | O | 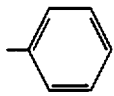 | 88–97 |
| 47 | CN | H | $-OC_2H_5$ | $-OC_2H_5$ | O | 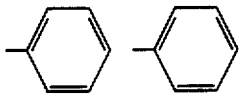 | 136–142 |
| 48 | CN | H |  | 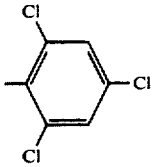 | O | 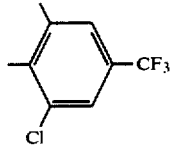 | 120 (decomposition) |
| 49 | CN | H | $-OC_2H_5$ | $-OC_2H_5$ | O | 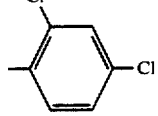 | 156 |
| 50 | CN | H | $-OC_2H_5$ | $-OC_2H_5$ | O | 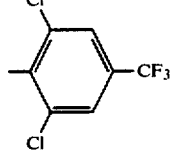 | 70 |
| 51 | H | H | $CH_3$ | $C_2H_5$ | O | 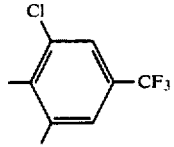 | 172 |
| 52 | $NO_2$ | H | $CH_3$ | $C_2H_5$ | O | 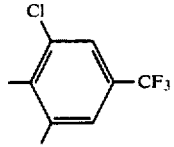 | 83 |
| 53 | H | H | $CH_3$ | $C_2H_5$ | O | 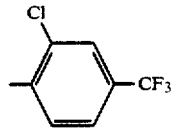 | 105 |
| 54 | H | H | $CH_3$ | $C_2H_5$ | O | 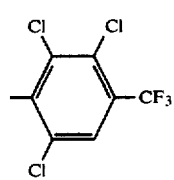 | 176 |

TABLE 2-continued
(I)
| Example No. | R | R¹ | R² | R³ | X | Ar | Melting point/°C. |
|---|---|---|---|---|---|---|---|
| 55 | H | H | CH₃ | C₂H₅ | O | 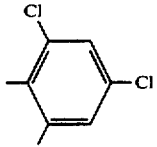 2,4,6-trichlorophenyl | 184 |
| 56 | NO₂ | H | CH₃ | C₂H₅ | O | 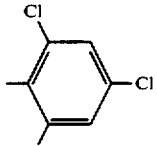 2,4,6-trichlorophenyl | 159 |
| 57 | H | H | CH₃ | —OC₂H₅ | O | 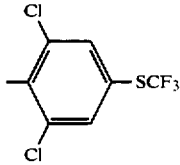 2,6-dichloro-4-SCF₃-phenyl | 165 |
| 58 | H | H | —OC₂H₅ | —OC₂H₅ | O | 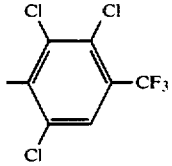 2,3,6-trichloro-4-CF₃-phenyl | 148 |
| 59 | H | H | —OC₂H₅ | —OC₂H₅ | O | 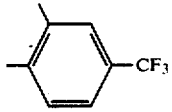 2-chloro-4-CF₃-phenyl | 103 |
| 60 | H | H | CH₃ | —OC₂H₅ | O | 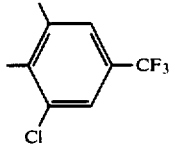 2,6-dichloro-4-CF₃-phenyl | 188 |
| 61 | H | H | CH₃ | —OC₂H₅ | O | 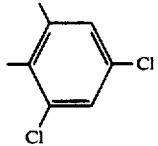 2,4,6-trichlorophenyl | 209 |
| 62 | H | H | CH₃ | —OC₂H₅ | O | 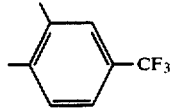 2-chloro-4-CF₃-phenyl | 143 |

TABLE 2-continued $$\text{(I)}$$

Structure: pyrazole with R at 4-position, N-Ar at N1, and at 5-position N(R¹)-P(=X)(R²)(R³)

| Example No. | R | R¹ | R² | R³ | X | Ar | Melting point/°C |
|---|---|---|---|---|---|---|---|
| 63 | H | H | CH₃ | —OC₂H₅ | O | 2,6-dichloro-4-(SO₂—CF₃)-phenyl | 205 |
| 64 | H | H | CH₃ | C₂H₅ | O | 2,6-dichloro-4-(SO₂—CF₃)-phenyl | 187 |
| 65 | H | H | —OC₂H₅ | —OC₂H₅ | O | 2,6-dichloro-4-(SCF₃)-phenyl | 154–157 |
| 66 | H | H | CH₃ | C₂H₅ | O | 2,6-dichloro-4-(SCF₃)-phenyl | 134 |
| 67 | H | H | CH₃ | C₂H₅ | O | 3,5-dichloropyridin-2-yl | ¹H—NMR: 1.55* |
| 68 | H | H | —OC₂H₅ | —OC₂H₅ | O | 3,4,5-trichloropyridin-2-yl | 117 |
| 69 | NO₂ | H | —OC₂H₅ | —OC₂H₅ | O | 3,5-dichloropyridin-2-yl | 106 |
| 70 | NO₂ | H | —OC₂H₅ | —OC₂H₅ | O | 2,3,6-trichloro-4-(CF₃)-phenyl | 101 |

TABLE 2-continued
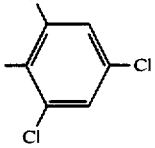
(I)
| Example No. | R | R¹ | R² | R³ | X | Ar | Melting point/°C. |
|---|---|---|---|---|---|---|---|
| 71 | $NO_2$ | H | $-OC_2H_5$ | $-OC_2H_5$ | O | 2,4,6-trichlorophenyl | 122 |
| 72 | $NO_2$ | H | $-OC_2H_5$ | $-OC_2H_5$ | O | 2-Cl-4-$CF_3$-phenyl | 115 |
| 73 | $NO_2$ | H | $CH_3$ | $-OC_2H_5$ | O | 2,4,6-trichlorophenyl | 126 |
| 74 | $NO_2$ | H | $CH_3$ | $-OC_2H_5$ | O | 2,6-diCl-4-$CF_3$-phenyl | 149 |
| 75 | $NO_2$ | H | $CH_3$ | $-OC_2H_5$ | O | 2-Cl-4-$CF_3$-phenyl | 162 |
| 76 | $NO_2$ | H | $CH_3$ | $-OC_2H_5$ | O | 2,6-diCl-4-$SO_2-CF_3$-phenyl | 106 |
| 77 | $NO_2$ | H | $CH_3$ | $C_2H_5$ | O | 2-Cl-4-$CF_3$-phenyl | 140 |
| 78 | $NO_2$ | H | phenyl | phenyl | O | 2,6-diCl-4-$CF_3$-phenyl | 204 |

TABLE 2-continued
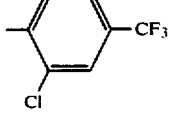
| Example No. | R | R¹ | R² | R³ | X | Ar | Melting point/°C. |
|---|---|---|---|---|---|---|---|
| 79 | $NO_2$ | H | —C₆H₅ | —C₆H₅ | O | 2,6-Cl₂-4-CF₃-C₆H₂ | 159 |
| 80 | H | H | $CH_3$ | $-OC_2H_5$ | O | 2,3-Cl₂-5-pyridyl | 146–147 |
| 81 | CN | H | —C₆H₅ | —C₆H₅ | O | 2,6-Cl₂-4-CF₃-C₆H₂ | 186–196 |
| 82 | CN | H | $-OC_2H_5$ | $-OC_2H_5$ | S | 2,4,6-Cl₃-C₆H₂ | 170–174 |
| 83 | CN | H | $-OC_2H_5$ | $-OC_2H_5$ | S | C₆H₅ | ¹H—NMR: 7.8* |
| 84 | CN | H | $-OC_2H_5$ | $-OC_2H_5$ | S | 2,6-Cl₂-4-SCF₃-C₆H₂ | 89–93 |
| 85 | CN | H | $-OC_2H_5$ | $-OC_2H_5$ | S | 2,3-Cl₂-5-pyridyl | 118 |
| 86 | CN | H | —C₆H₅ | —C₆H₅ | O | 2,3-Cl₂-5-pyridyl | 84 (decomposition) |
| 87 | CN | H | —C₆H₅ | —C₆H₅ | O | 2-Cl-4-OCF₃-C₆H₃ | 195–200 |

TABLE 2-continued
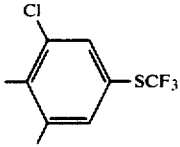
(I)
| Example No. | R | R¹ | R² | R³ | X | Ar | Melting point/°C |
|---|---|---|---|---|---|---|---|
| 88 | CN | H | –C₆H₅ | –C₆H₅ | O | 2,6-Cl₂-4-SCF₃-C₆H₂ | 131 |
| 89 | H | H | CH₃ | –OCH₃ | O | 2,6-Cl₂-4-CF₃-C₆H₂ | 150–156 |
| 90 | CN | H | CH₃ | –OC₂H₅ | O | 2,6-Cl₂-4-CF₃-C₆H₂ | 212–214 |
| 91 | H | H | –OC₂H₅ | –OC₂H₅ | O | 2,6-Cl₂-4-OCF₃-C₆H₂ | 141 |
| 92 | H | H | –C₆H₅ | –C₆H₅ | O | 2-Cl-4-CF₃-C₆H₃ | 135 |
| 93 | NO₂ | H | CH₃ | –C₆H₅ | O | 2,3,5-Cl₃-4-CF₃-C₆H | 105 |
| 94 | NO₂ | H | –C₆H₅ | –C₆H₅ | O | 2-Cl-4-CF₃-C₆H₃ | 164 |
| 95 | H | H | CH₃ | –OCH₃ | O | 2,3,5-Cl₃-4-CF₃-C₆H | 185–188 |

TABLE 2-continued
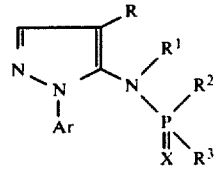
(I)
| Example No. | R | R¹ | R² | R³ | X | Ar | Melting point/°C. |
|---|---|---|---|---|---|---|---|
| 96 | CN | H | CH₃ | —OCH₃ | S | 2,6-Cl₂-4-CF₃-C₆H₂ | 99–106 |
| 97 | CN | H | CH₃ | C₆H₅ | O | 2,6-Cl₂-4-CF₃-C₆H₂ | 203 |
| 98 | CN | H | CH₃ | —OC₂H₅ | S | 2,6-Cl₂-4-CF₃-C₆H₂ | 109–114 |
| 99 | NO₂ | H | —OC₂H₅ | —OC₂H₅ | S | 2,6-Cl₂-4-CF₃-C₆H₂ | 80–84 |
| 100 | NO₂ | H | C₂H₅ | —OCH₃ | S | 2,6-Cl₂-4-CF₃-C₆H₂ | 108–113 |
| 101 | NO₂ | H | CH₃ | —OCH₃ | O | 2,6-Cl₂-4-CF₃-C₆H₂ | 135 |
| 102 | CN | H | C₂H₅ | —OCH₃ | S | 2,6-Cl₂-4-CF₃-C₆H₂ | 118–125 |
| 103 | CN | H | C₂H₅ | —OCH₃ | S | C₆H₅ | 103–106 |

TABLE 2-continued

| Example No. | R | R¹ | R² | R³ | X | Ar | Melting point/°C |
|---|---|---|---|---|---|---|---|
| 104 | CN | H | $CH_3$ | —$OCH_3$ | S | phenyl | 131 |
| 105 | H | H | $CH_3$ | —$OCH_3$ | O | 2,6-dichloro-4-$OCF_3$-phenyl | 98 |
| 106 | H | H | phenyl | phenyl | O | 2,6-dichloro-4-$OCF_3$-phenyl | 95 |
| 107 | H | H | phenyl | phenyl | O | 2,3,6-trichloro-4-$CF_3$-phenyl | 158 |
| 108 | H | H | phenyl | phenyl | O | 2,6-dichloro-4-$CF_3$-phenyl | 178 |
| 109 | H | H | $CH_3$ | pyridyl | O | 2,3,6-trichloro-4-$CF_3$-phenyl | 170 |
| 110 | $NO_2$ | H | $C_2H_5$ | —O-phenyl | S | 2,6-dichloro-4-$CF_3$-phenyl | 122 |
| 111 | $NO_2$ | H | $C_2H_5$ | —O-phenyl | O | 2,3,6-trichloro-4-$CF_3$-phenyl | 112 |

TABLE 2-continued
$$\text{(1)}$$
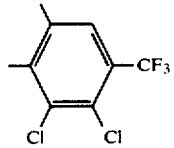
| Example No. | R | R¹ | R² | R³ | X | Ar | Melting point/°C |
|---|---|---|---|---|---|---|---|
| 112 | $NO_2$ | H | $C_2H_5$ | —$OCH_3$ | S | 2,4-Cl, 3-Cl, 5-$CF_3$-phenyl | 117 |
| 113 | $NO_2$ | H | $C_2H_5$ | —$OCH_3$ | S | 2-Cl, 4-$CF_3$-phenyl | 144 |
| 114 | $NO_2$ | H | —$OC_2H_5$ | —$OC_2H_5$ | S | 2-Cl, 4-$CF_3$-phenyl | 82 |
| 115 | $NO_2$ | H | $CH_3$ | —$OCH_3$ | S | 2,4-Cl, 3-Cl, 5-$CF_3$-phenyl | 101 |
| 116 | H | H | $CH_3$ | —$OCH_3$ | O | pentafluoro-$CF_3$-phenyl | 147 |
| 117 | H | H | $CH_3$ | phenyl | O | pentafluoro-$CF_3$-phenyl | 169 |
| 118 | H | H | $CH_3$ | —$OCH_3$ | O | 2-Cl, 4-CF-phenyl | 162 |
| 119 | $NO_2$ | H | $CH_3$ | —$OCH_3$ | O | 2-Cl, 4-$CF_3$-phenyl | 204 |

TABLE 2-continued
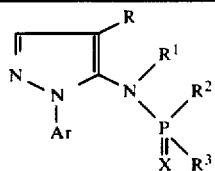
(I)
| Example No. | R | R¹ | R² | R³ | X | Ar | Melting point/°C. |
|---|---|---|---|---|---|---|---|
| 120 | NO₂ | H | CH₃ | phenyl | O | 2,3,5,6-tetrafluoro-4-CF₃-phenyl | 157 |
| 121 | NO₂ | H | CH₃ | —OCH₃ | O | 2,3,5,6-tetrafluoro-4-CF₃-phenyl | 171 |
| 122 | NO₂ | H | CH₃ | —OCH₃ | S | 2,3,5,6-tetrafluoro-4-CF₃-phenyl | 134 |
| 123 | NO₂ | H | —OC₂H₅ | —OC₂H₅ | S | 2,3,5,6-tetrafluoro-4-CF₃-phenyl | 104 |
| 124 | NO₂ | H | CH₃ | —OC₃H₇—i | O | 2,6-dichloro-4-CF₃-phenyl | 128 |
| 125 | CN | H | —OC₂H₅ | —OC₂H₅ | O | 2,4,6-trichlorophenyl | 205 |
| 126 | CN | H | CH₃ | —OCH₃ | O | 2,6-dichloro-4-CF₃-phenyl | 219–23 |
| 127 | CN | H | C₂H₅ | —OCH₃ | S | 2,4,6-trichlorophenyl | 147–53 |

TABLE 2-continued
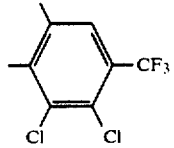
(I)
| Example No. | R | R¹ | R² | R³ | X | Ar | Melting point/°C. |
|---|---|---|---|---|---|---|---|
| 128 | NO₂ | H | CH₃ | —OCH₃ | O | 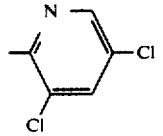 | 85 |
| 129 | CN | H | —OC₂H₅ | —OC₂H₅ | O | 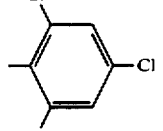 | 150–52 |
| 130 | CN | H | CH₃ | —OCH₃ | S | 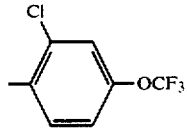 | 125–29 |
| 131 | CN | H | CH₃ | —OCH₃ | S | 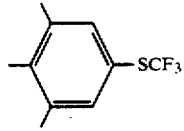 | 94–96 |
| 132 | CN | H | CH₃ | —OCH₃ | S | 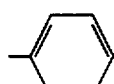 | 137–40 |
| 133 | CN | H | CH₃ | —OC₂H₅ | S | 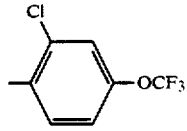 | 92–95 |
| 134 | CN | H | C₂H₅ | —OCH₃ | S | 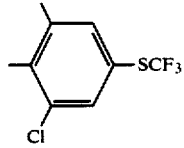 | 125–28 |
| 135 | CN | H | CH₃ | —OCH₃ | O | 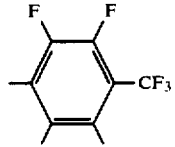 | 206–12 |
| 136 | H | H | CH₃ | —OC₂H₅ | O |  | 106–09 |

TABLE 2-continued (I)

| Example No. | R | R¹ | R² | R³ | X | Ar | Melting point/°C. |
|---|---|---|---|---|---|---|---|
| 137 | NO$_2$ | H | CH$_3$ | —OC$_2$H$_5$ | O | 2,3,5,6-tetrafluoro-4-CF$_3$-phenyl | 01 |
| 138 | NO$_2$ | H | —OC$_2$H$_5$ | —OC$_2$H$_5$ | O | 2,3,5,6-tetrafluoro-4-CF$_3$-phenyl | 01 |
| 139 | CN | H | CH$_3$ | —OCH$_3$ | O | phenyl | 164–65 |
| 140 | CN | H | CH$_3$ | —OCH$_3$ | O | 2,4-dichloro-phenyl (with Cl) | 215–18 |
| 141 | CN | H | C$_2$H$_5$ | —OCH$_3$ | S | 2,6-dichloro-4-SCF$_3$-phenyl | 115–17 |
| 142 | CN | H | CH$_3$ | —OCH$_3$ | O | 2-chloro-4-OCF$_3$-phenyl | 176–79 |
| 143 | NO$_2$ | H | C$_2$H$_5$ | —OCH$_3$ | S | 2,3,5,6-tetrafluoro-4-CF$_3$-phenyl | 112–15 |
| 144 | NO$_2$ | Na | CH$_3$ | —OCH$_3$ | O | 2,6-dichloro-3-CF$_3$-4-Cl-phenyl | >300 |

TABLE 2-continued

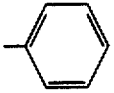

| Example No. | R | R¹ | R² | R³ | X | Ar | Melting point/°C |
|---|---|---|---|---|---|---|---|
| 145 | $NO_2$ | Na | $CH_3$ | phenyl | O | 2,4,6-trichloro-3-CF₃-phenyl | >300 |
| 146 | $NO_2$ | Na | $CH_3$ | phenyl | O | 2,4-dichloro-3-CF₃-phenyl | >300 |

*The ¹H—NMR spectra were recorded in $CDCl_3$ with tetramethylsilane as the internal standard. The chemical shift as the δ value in ppm is quoted.

USE EXAMPLES

The compound shown below was employed as the comparison substance in the following use examples:

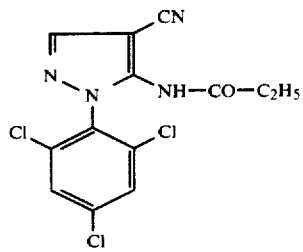

(A)

4-cyano-5-propionamido-1-(2,4,6-trichlorophenyl)-pyraole (known from DE-OS (German Published Specification) No. 3,226,513).

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

In this test, a clearly superior activity and selectivity towards useful plants compared to that of comparison substance A is shown, for example, by the compounds according to preparation Examples 74 and 76.

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 L of water/ha. After three weeks, the degree of damage to the plants is rated in % damage in comparison to the development of the untreated control.

In this test, a clearly superior activity and selectivity towards useful plants compared to that of comparison substance A is shown, for example, by the compounds according to preparation Examples 3, 74 and 76.

It will be understood that the specification and examples are illustrative but not limitative of the present invention and that other embodiments within the spirit and scope of the invention will suggest themselves to those skilled in the art.

We claim:

1. A substituted 5-amino-1-arylpyrazole of the formula

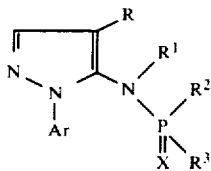

in which
- R represents hydrogen, cyano or nitro, or represents straight-chain or branched alkoxycarbonyl with 1 to 4 carbon atoms,
- R¹ represents hydrogen, or represents straight-chain or branched alkyl with 1 to 6 carbon atoms,
- R² and R³ independently of one another represent in each case straight-chain or branched alkyl, alkenyl or alkinyl with in each case up to 8 carbon atoms, or represent straight-chain or branched halogenoalkyl with 1 to 6 carbon atoms and 1 to 13 identical or different halogen atoms, or represent straight-chain or branched alkoxyalkyl with in each case 1 to 4 carbon atoms in the individual alkyl parts, or represent straight-chain or branched alkoxy with 1 to 6 carbon atoms, or represent cycloalkyl or cycloalkyloxy with in each case 3 to 7 carbon atoms, or represent aryl, aryloxy, aralkyl or aralkyloxy with in each case 6 to 10 carbon atoms in the individual aryl parts and, where appropriate, one to three carbon atoms in the straight-chain or branched alkyl parts, in each case optionally monosubstituted or polysubstituted in the aryl part by identical or different substituents selected from the group consisting of halogen, cyano, nitro and in each case straight-chain or branched alkyl, alkoxy, alkylthio or halogenoalkyl with in each case 1 to 4 carbon atoms and, in the case of the halogenoalkyl, with 1 to 9 identical or different halogen atoms,
- X represents oxygen or sulphur, and
- Ar represents phenyl, 2-pyridyl, 3-pyridyl or 4-pyridyl, in each case optionally monosubstituted or polysubstituted by identical or different substituents selected from the group consisting of cyano, nitro, halogen, in each case straight-chain or branched alkyl, alkoxy and alkoxycarbonyl with in each case 1 to 4 carbon atoms in the alkyl part, in each case straight-chain or branched halogenoalkyl and halogenoalkoxy with in each case 1 to 4 carbon atoms and 1 to 9 identical or different halogen atoms or the radical —S(O)ₙ—R⁴, wherein
- R⁴ represents amino, or represents in each case straight-chain or branched alkyl, alkylamino, dialkylamino or halogenoalkyl with in each case 1 to 4 carbon atoms in the individual alkyl parts and, in the case of the halogenoalkyl, with 1 to 9 identical or different halogen atoms, and
- n represents the number 0, 1 or 2, or a salt thereof.

2. A substituted 5-amino-1-aryl-pyrazole or salt according to claim 1, in which
- R represents hydrogen, cyano, nitro, methoxycarbonyl or ethoxycarbonyl,
- R¹ represents hydrogen, methyl, ethyl, n- or i-propyl, or n-, i- or s-butyl,
- R² and R³ independently of one another each represent methyl, ethyl, n- or i-propyl, n-, or i-, s- or t-butyl, allyl, propargyl, chloromethyl, dichloromethyl, trichloromethyl, fluoromethyl, dichlorofluoromethyl, trifluoromethyl, dichlorofluoromethyl, difluorochloromethyl, chloroethyl, trichloroethyl, pentachloroethyl, trifluoroethyl, pentafluoroethyl, bromoethyl, methoxymethyl, methoxyethyl, ethoxymethyl, ethoxyethyl, n-propoxymethyl, i-propoxymethyl, n-propoxyethyl, i-propoxyethyl, methoxy, ethoxy, n- or i-propoxy, n-, i-, s- or t-butoxy, cyclopropyl, cyclopentyl, cyclohexyl or cyclohexyloxy, or represent benzyl, benzyloxy, phenyl or phenoxy, in each case optionally mono-, di-, tri-, tetra- or pentasubstituted by identical or different substituents selected from the group consisting of fluorine, chlorine, bromine, cyano, nitro, methyl, ethyl, methoxy, methylthio or trifluoromethyl,
- Ar represents phenyl which is optionally mono-, di-, tri-, tetra- or pentasubstituted by identical or different substituents, or represents 2-pyridyl which is optionally mono-, di-, tri- or tetrasubstituted by identical or different substituents, and the substituents in each case being selected from the group consisting of cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trilfuoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroerthoxy, trifluoroethoxy, difluorodichloroethoxy, trifluorodichloroethoxy, pentachloroethoxy or the radical —S(O)ₙ—R⁴, wherein
- R⁴ represents amino, methylamino, ethylamino, dimethylamino, diethylamino, fluorodichloromethyl, difluoromethyl, tetrafluoroethyl, trichloroethyl, trifluoromethyl, methyl or ethyl and
- n represents the number 0, 1 or 2.

3. A compound according to claim 1 wherein such compound is 5-(methyl-phenyl-phosphinylamino)-1-(2-chloro-4-trifluoromethyl-phenyl)-4-nitro-pyrazole of the formula

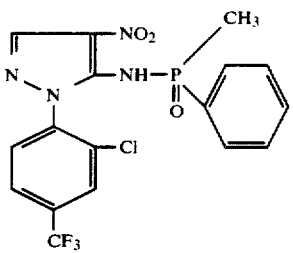

or an alkali metal salt thereof.

4. A compound according to claim 1 wherein such compound is 5-(methyl-phenyl-phosphinylamino)-1-(2,3,6-trichloro-4-trifluoromethyl-phenyl)-4-nitro-pyrazole of the formula

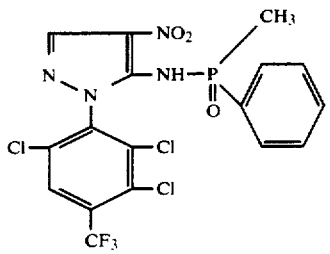

or an alkali metal salt thereof.

5. A compound according to claim 1 wherein such compound is 5-(O-methyl-methyl-phosphonylamino)-1-(2,3,6-trichloro-4-trifluoromethyl-phenyl)-4-nitro-pyrazole of the formula

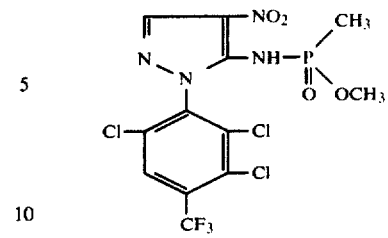

or an alkali metal salt thereof.

6. A herbicidal composition comprising a herbicidally effective amount of a compound or salt according to claim 1 and a diluent.

7. A method of combating unwanted vegetation which comprises applying to such vegetation or to a locus from which it is desired to exclude such vegetation a herbicidally effective amount of a compound or salt according to claim 2.

8. The method according to claim 7, wherein such compound is
5-(methyl-phenyl-phosphinylamino)-1-(2-chloro-4-trifluoromethyl-phenyl)-4-nitro-pyrazole,
5-(methyl-phenyl-phosphinylamino)-1-(2,3,6-trichloro-4-trifluoromethyl-phenyl)-4-nitro-pyrazole or
5-(O-methyl-methyl-phosphonylamino)-1-(2,3,6-trichloro-4-trifluoromethyl-phenyl)-4-nitro-pyrazole, or a salt thereof.

* * * * *

UNITED STATES PATENT AND TRADEMARK OFFICE
CERTIFICATE OF CORRECTION

PATENT NO. : 4,695,308

DATED : September 22, 1987

INVENTOR(S) : Reinhold Gehring, et al.

Page 1 of 2

It is certified that error appears in the above-identified patent and that said Letters Patent is hereby corrected as shown below:

| | |
|---|---|
| Title Page, under "Foreign Application Priority Data" | Delete "Nov. 5, 1985" and substitute --Nov. 9, 1985-- |
| Col. 3, lines 45, 55; Col. 58, line 57 | Correct --aryl-pyrazoles-- |
| Col. 3, lines 52-53 | Correct spelling of --herbicidal-- |
| Col. 16, line 20 | After "can" insert --also-- |
| Col. 17, line 5 | Delete "catalyst" and substitute --catalysts-- |
| Col. 18, line 8 | Delete "whereby" and substitute --where-- |
| Col. 18, lines 29-30 | Correct spelling of --Eleusine-- |
| Col. 18, line 31 | Correct spelling of --Sagittaria-- |
| Col. 19, line 40 | Delete "ther" and substitute --there-- |
| Col. 21, line 59 | Delete "aded" and substitute --added-- |
| Col. 22, lines 31, 50 | Delete "phenyl)pyrazole" and substitute --phenyl)-pyrazole-- |
| Col. 23, Example 6, first formula under "$R^3$" | Delete "-OC$_6$H$_5$" and substitute -- -OC$_2$H$_5$ -- |
| Col. 47, last line under "$R^3$" | Delete "O" and substitute --S-- |
| Col. 50, 7th formula under "Ar" | Delete "-CF" and substitute -- -CF$_3$ -- |

UNITED STATES PATENT AND TRADEMARK OFFICE
CERTIFICATE OF CORRECTION

PATENT NO. : 4,695,308

DATED : September 22, 1987

INVENTOR(S) : Reinhold Gehring, et al.

It is certified that error appears in the above-identified patent and that said Letters Patent is hereby corrected as shown below:

Column 56, lines 1 and 2   Delete "01" and substitute --01''--
under "Melting Point/°C."

Signed and Sealed this

Fourteenth Day of June, 1988

Attest:

DONALD J. QUIGG

*Attesting Officer*     *Commissioner of Patents and Trademarks*